United States Patent [19]

Tanaka et al.

[11] Patent Number: 4,838,789

[45] Date of Patent: Jun. 13, 1989

[54] MATERIAL PACKS FOR PREPARING PLATE DENTURES

[75] Inventors: Hisatoshi Tanaka, Morioka; Masao Abiru, Omiya, both of Japan

[73] Assignee: G-C Dental Industrial Corp., Tokyo, Japan

[21] Appl. No.: 102,856

[22] Filed: Sep. 30, 1987

[30] Foreign Application Priority Data

Oct. 17, 1986 [JP] Japan .................. 61-245424

[51] Int. Cl.⁴ .............................. A61C 13/08
[52] U.S. Cl. ...................... 433/171; 433/37
[58] Field of Search ............ 433/37, 171, 167, 168.1, 433/196

[56] References Cited

U.S. PATENT DOCUMENTS 3,621,575 11/1971 Schneider et al. ............... 433/171
4,553,936 11/1985 Wang ...................... 433/37
4,746,469 5/1988 Yamashita .................. 433/37

Primary Examiner—Gene Mancene
Assistant Examiner—Adriene J. Lepiane
Attorney, Agent, or Firm—Oblon, Spivak, McClelland, Maier & Neustadt

[57] ABSTRACT

A material pack for the preparation of plate dentures comprises an outer pack formed of a material capable of shielding active energy beams, on which the necessary particulars are specified including the size and form of the jaws, the size, form and color tone of artificial teeth and the color tone of a photopolymerizable resin and the outer pack containing therein a matrix formed of a light transmitting material, the artificial teeth provided on the matrix while a part thereof projecting from the matrix, and the photopolymerizable resin provided inside of the matrix. The matrix may be coated thereon with a material capable of shielding active energy beams.

2 Claims, 1 Drawing Sheet

MATERIAL PACKS FOR PREPARING PLATE DENTURES

BACKGROUND OF THE INVENTION

A material pack for the preparation of plate dentures comprises an outer pack formed of a material capable of shielding active energy beams. The outer pack contains a matrix formed of a light transmitting material, a photopolymerizable resin provided inside of the matrix, and artificial teeth provided on the matrix while a part thereof projects from the matrix into the photopolymerizable resin such that the artificial teeth are finely adjustable. The necessary particulars including, the size and form of the matrix, the size, form and color tone of the artificial teeth and the color tone of the photopolymerizable resin are specified on the outer pack.

1. Field of the Invention

The present invention relates to a material pack for the preparation of plate dentures, which makes it possible to prepare within a very short period of time a plate denture that is accommodative to the perculiarity of an individual, excels in fitting accuracy and aesthetics.

2. Statement of the Prior Art

Hitherto, plate dentures were prepared by making a wax denture based on a working model on which the oral mouth state of an individual was reproduced, and replacing the wax denture by a resin. Thus, since the process required for completing the plate denture was very lengthy, it took a period of as long as several weeks for an individual to obtain the completed plate denture. In the meantime, the individual had to live a toothless life.

General plate dentures relying upon a thermally polymerizable resin were prepared in the following manner. In order to reproduce the intra-mouth state of an individual on a working model, preliminary impression taking, preparation of a gypsum model, preparation of an individual tray, trying of the individual tray in the oral mouth, functional impression taking, preparation of the working model and correction of the form of the working model were first carried out. Then, preparation of a bite plate, bite taking, attachment of the bite plate to an articulator, arrangement of artificial teeth, trying and correction of a wax denture in the oral mouth and formation of gingival portion were carried out to make the wax denture. For subsequent replacement of the wax denture by the thermally polymerizable resin, investment of the wax denture, wax washing out, application of a resin separator, making the resin doughing, the resin filling, polymerization of the resin, and removal and polishing of the polymerized denture were conducted. Thus, a number of the steps were so many that it took a period of as long as several weeks for an individual to obtain the completed plate denture.

Many studies were made with a view to shortening the period of time needed for the preparation of plate dentures. In particular, there were proposed plate dentures designed for temporary use (hereinafter referred to as the temporary denture). In order to prepare the temporary dentures within a very short period of time, Japanese Patent Publication No. 46-24868, U.S. Pat. Nos. 3,460,252 and 3,621,575 disclose a combination of a temporary plate having a temporary arrangement of artificial teeth with a self-curing resin.

More specifically, the temporary plate having a temporary arrangement of artificial teeth provided in a matrix of the jaw form prepared using the average intra-mouth form as the model and formed of wax or polyethylene (hereinafter called the matrix) is used in combination with the self-curing resin. In order to prepare the temporary denture, the temporary plate having a temporary arrangement of artificial teeth is pressed against a gypsum model for adjustment. Afterwards, the self-curing resin is placed on the inside portion of the temporary plate forming the plate body, and the assembly is put over an objective, the impression of which is to be taken, followed by setting or curing by polymerization (hereinafter simply referred to as the polymerization or curing). The matrix portion is finally removed, and form adjustment is carried out to obtain the temporary denture.

The preparation of the temporary denture comprising a combination of the temporary plate having a temporary arrangement of artificial teeth with the self-curing resin is quite different from the aforesaid preparation of plate dentures relying upon the thermally polymerizable resin, and has an advantage thereover in that the finished temporary denture is available within a very short period of time, since the time needed for completing it is about 1 hour. However, any attention is hardly paid to fitting accuracy of the temporary denture with respect to the mucosal surface of the oral mouth, aesthetics of appearance such as the selection of artificial teeth and difficulty encountered in using the self-curing resin. Thus, the conventional temporary denture is still unsatisfactory due to its poor fitting accuracy with respect to the mucosal surface of the oral mouth and its cheap appearance.

Use of the self-curing resin also leads to various disadvantages in view of manipulations.

The disadvantages derived from the preparation of the temporary denture comprising a combination of the temporary plate having a temporary arrangement of artificial teeth with the self-curing resin are considered to be caused by the following reasons.

Since setting of the self-curing resin proceeds at room temperature, it sometimes occurs so prematurely that a time period allowed for manipulations such as muscle formation and centric relation biting is insufficient. It is difficult to carry out reliable fitting manipulation within a limited period of time of several minutes during which that resin is set.

In the course of this manipulation, setting of the self-curing resin placed inside of the temporary plate having a temporary arrangement of artificial teeth may come to an end. In this case, considerable time should be spent for removal of the set resin deposits, or a new temporary plate having a temporary arrangement of artificial teeth must be used.

Further, the polymerization of the self-curing resin generates the heat of reaction, which tends to deform the matrix portion of the temporary plate having a temporary arrangement of artificial teeth and formed of wax or polyethylene. In addition, since that heat of reaction causes the resin placed inside of the temporary plate to be set within a short time, air bubbles tend to occur on the application surface for impression taking or in narrow portions such as the portions of contact of the artificial teeth and the matrix portion with the resin. Such bubbles do not only cause the deposition of contaminants on the temporary denture during use, but also spoil the aesthetic appearance thereof. Still further, when the self-curing resin is directly pressed against the oral mouth in the doughing form, there is a fear that unpolymerized monomers may irritate the mucosa of the oral mouth. Still further, the artificial teeth used with the temporary plate having a temporary arrangement of artificial teeth is unsatisfactory in terms of their aesthetic appearance, since they cannot freely be selected according to individuality due to some limitations imposed upon the form, color tone and size thereof. Still further, since the artificial teeth are fixed in place in the matrix and, hence, cannot be adjusted finely with respect to the antagonists, their occlusal relation to the antagonists remains unsatisfactory.

As mentioned above, while the temporary denture comprising a combination of the temporary plate having a temporary arrangement of artificial teeth with the self-curing resin has the advantages that it can be prepared within a very short time, the obtained temporary denture has a number of disadvantages in terms of its fitting accuracy with respect to the mucosal surface of the oral mouth, aesthetics, or occlusal relation and manipulation properties. In other words, as good as the conventional temporary denture is in view of preparation alone, it is still considered to have its disadvantages.

SUMMARY OF THE INVENTION

As a result of intensive and extensive studies made for the purpose of preparing within a very short time a denture which excels in fitting accuracy and aesthetics, that purpose is achieved by the provision of a material pack for the preparation of plate dentures, which contains therein a photopolymerizable resin.

DETAILED EXPLANATION OF THE INVENTION

The material pack for the preparation of plate dentures according to the present invention is understood to comprise an outer pack containing therein a matrix previously formed of a light transmitting plastic material into the denture base form, an arrangement of artificial teeth previously provided along the alveolar arch, a part of said teeth projecting from said matrix, and a photopolymerizable resin filled inside of said matrix. In order to accord with the oral mouths of individuals, the matrices may take on various sizes such as extra small, small, medium, large and extra large sizes, and assume various forms such as tapering, square and ovoid forms. The artificial teeth may also assume various forms such as tapering, square, ovoid, square-tapering, short square, vigorous-square and vigorous-square-tapering forms, and be of various color tones and sizes. The photopolymerizable resins of various color tones may be provided for.

Specified on the outer pack portion of each material pack according to the present invention are the aforesaid particulars, i.e., the size and form of the matrix, the size, form and color tone of the artificial teeth and the color tone of the photopolymerizable resin. Hence, it is easy for an operator to select the material pack accommodative to an individual. By separately providing various matrices of various sizes and forms for the material packs for the preparation of dentures for the purpose of try-in, it is easier to select the material pack accommodative to an individual. It is to be understood that the outer pack portion of each material pack is required to be formed of a material capable of shielding active energy beams so as to shield unnecessary active energy beams such as natural rays and thereby improve storability. By coating a material capable of shielding active energy beams on the outside of the matrix of each material pack, it is possible to make effective use of the reflection of active energy beams irradiated to polymerize the resin and thereby improve the efficiency of irradiation. An opening for the admission of active energy beams may be provided on the matrix so as to set the resin. When no opening for the admission of active energy beams is provided on the matrix, a part of the coating may be removed or cut out for the irradiation of active energy beams to cure the resin.

Further since a part of each artificial tooth is projected from the matrix and, hence, when bite taking, fine adjustment for occlusal relation can be made between antagonists teeth.

In general, the preparation of plate dentures with the material packs for the preparation of plate dentures according to the present invention comprises the steps of:

taking a preliminary impression with an impression material, pouring gypsum slurry into the obtained preliminary impression to make a gypsum model, selecting a matrix of the size and form bearing resemblance to the size and form of the jaws, and pressing it against the gypsum model, while adjusting peripheries, mucosal surface, intermaxillary distance, occlusal surface, base surface of artificial teeth and the like, attaching the thus adjusted matrix to an objective for impression taking to take an impression, irradiating the photopolymerizable resin with active energy beams and polymerizing the photopolymerizable resin after form regulation, and removing the matrix portion followed by finish polishing.

Thus, it is possible to prepare within a very short time a plate denture which is accommodative to the peculiarity of an individual, excels in fitting accuracy and aesthetics.

As the photopolymerizable resins used in the preparation of plate dentures with the use of the material pack of the present invention, use may be made of any resin which is polymerized by the irradiation of active energy beams. It is to be understood, however, that the catalyst for chemical polymerization may optionally be used in combination with the photopolymerizable resin, as the occasion may be. Unlike a self-curing resin relying upon chemical polymerization alone, because self-curing resin is apt to set too fast but the photopolymerizable resin is unlikely to set or cure prematurely. Hence, it is possible to conduct manipulations such as muscle formation and centric relation occulsion in a sufficiently careful manner without paying attention to curing time, and take precise impressions, whereby the fitting accuracy of the completed plate denture is improved.

As is not the case with the self-curing resin, the photopolymerizable resin is not possibly cured in the course of impression-taking. Further, the photopolymerizable resin may not possibly deform the matrix portion, since it generates only a limited amount of the heat of reaction during its polymerization. Still further, the photopolymerizable resin is not polymerized, unless it is exposed to active energy beams, and shows relatively constant flowability during press-fitting, as compared with the self-curing resin, so that the denture having more improved fitting accuracy can be obtained. Still further, since the photopolymerizable resin previously filled inside of the matrix is freely controllable in terms of setting, unlike the conventional self-curing resin, defoaming may occasionally be effected. Hence, it is possible to completely suppress foaming responsible for the deposition of contaminants on the plate denture.

The material for the matrix portion used in the present invention may be any light transmitting material represented by plastics, wax and glass. In view of manipulations and inexpensive production, however, preference is given to plastics because of their excellent light transmission properties. The usable plastics may be of the thermoplastic or thermosetting type. Desired plastics excelling in light transmission properties include, for instance, polyethylene, polypropylene, polybutylene, polystyrene, vinyl acetate, polyacrylate, polyvinyl chloride, polyvinylidene chloride, polyacrylonitrile, polyvinyl ether, polyvinyl ketone, polyether, polyester, polyamide, polycarbonate, polyvinyl alcohol, polyvinyl acetal, polyurethane or polysulfone and derivatives thereof. If required, the matrix may be provided on the outside with an opening for the admission of active energy beams. Alternatively, the matrix may be coated on the outside with a metal foil or the like for the purpose of preventing scattering of active energy beams and reflecting them, and the thus obtained coating may partly be removed to form an opening through which the active energy beams are irradiated.

The photopolymerizable resin used in the present invention may comprise a polymerizable ethylenical compound having at least one ethylenically unsaturated double bond, a photopolymerization initiator, a photosensitizer and a filler, and is polymerized upon exposure to active energy beams.

By the "ethylenical compound" is meant a compound having in its chemical structure at least one ethylenically unsaturated double bond, which takes on the chemical forms such as monomers, prepolymers (i.e., dimers, trimers and other oligomers), and mixtures and copolymers thereof.

More specifically, the monomers having one ethylenically unsaturated double bond include methyl methacrylate and acrylate, ethyl methacrylate and acrylate, isopropyl methacrylate and acrylate, hydroxyethyl methacrylate and acrylate, tetrahydrofulfuryl methacrylate and acrylate, and glycidyl methacrylate and acrylate; the monomers having two ethylenically unsaturated double bonds include aromatic ones such as 2,2-bis(methacryloxyphenyl)propane, 2,2-bis[4-(2-hydroxy-3-methacryloxyphenyl)]propane, 2,2-bis(4-methacryloxyethoxyphenyl)propane, 2,2-bis(4-methacryloxydiethoxyphenyl)propane and 2,2-bis(4-methacryloxypropoxyphenyl)propane as well as acrylate analogues thereof and aliphatic ones such as ethylene glycol dimethacrylate, diethylene glycol dimethacrylate, triethylene glycol dimethacrylate, butylene glycol dimethacrylate, neopentyl glycol dimethacrylate, polypropylene glycol dimethacrylate, 1,3-butanediol dimethacrylate, 1,4-butanediol dimethacrylate and 1,6-hexanediol dimethacrylate as well as acrylate analogues thereof. As the monomers having three ethylencially unsaturated double bonds, mentioned are trimethylolpropane trimethacrylate, trimethylolethane trimethacrylate, pentaerythritol trimethacrylate and trimethylolmethane methacrylate as well as acrylate analogues thereof, and as the monomers having four ethylenically unsaturated double bonds, mentioned are pentaerythritol tetramethacrylate and pentaerythritol tetraacrylate as well as urethane monomers such as urethane diacrylate and urethane dimethacrylate.

The photopolymerization initiators used include, for instance, benzoin, benzoin alkyl ether, benzophenone, acetophenone and their derivatives, tioxantone and its derivatives, benzyl, camphor quinones, alpha-naphtyl, acenaphthane, p,p'-dimethoxybenzyl and p,p'-dichlorobenzyl.

The photosensitizers used include, for instance, dimethylaminoethyl methacrylate, n-butylamine, triethylamine, triethyl-n-butylphosphine, and 4-dimethylaminobenzoic acid isoamyl.

The fillers used may be an inorganic and/or organic filler. For instance, use may be made of the so-called composite filler obtained by compacting with a polymer quartz powders, alumina powders, glass powders, kaolin, talc, calcium carbonate, barium aluminosilicate glass, titanium oxide, borosilicate glass, colloidal silica powders or colloidal silica and pulverizing the obtained compact. As the polymer powders, methyl polyacrylate, methyl polymetacrylate, ethyl polymethacrylate, methyl methacrylate-ethyl methacylate copolymers, crosslinked type methyl polymethacrylate and etylene-vinyl acetate copolymers may be used, for instance. Alternatively, these polymer powders may be used in admixtures with the aforesaid inorganic powders.

It is preferred that, prior to mixing of the aforesaid inorganic filler with a binder resin, such a filler be previously treated with a coupling agent capable of reacting with both the filler and the binder resin.

As the coupling agent, use may be made of a silane coupling agent, a titanate coupling agent and an aluminate coupling agent, for instance. Alternatively, the inorganic filler may be grafted on the surface for bonding to the binder resin.

As the silane coupling agents, use may be made of, for instance, gamma-methacryloxypropyl trimethoxy silane, vinyltrichlorosilane, vinyl-tris(beta-methoxyethoxy)silane, gammamethacryloxypropyl methyldimethoxy silane, gamma-glycidoxypropyl trimethoxy silane, gamma-chloropropyl trimethoxy silane, beta-(3,4-epoxycyclohexyl)ethyl trimethoxy silane, trimethylchlorosilane, dimethyldichlorosilane, hexamethyldisilane, gamma-aminopropyl triethoxy silane, N-beta-(aminoethoxy)-gamma-aminopropyl trimethoxy silane and gamma-urenoidpropyl trimethoxy silane.

The surface treatment with such coupling agents is not limited to any specific manner, and may be carried out in a suitable manner. The amount of such a surface treatment agent varies depending upon the required properties, and are thus not generally determined. In general, however, that surface treatment agent may suitably be used in an amount of 0.1 to 20% by weight, preferably 1 to 10% by weight, with respect to the inorganics applied.

The active energy beams used in the present invention may be either one of visible rays or ultraviolet rays. Alternatively, active energy beams containing both visible and ultraviolet rays in their spectra may be employed. Wavelengths of 240 to 600 nm are preferred. Applicable light sources are represented by carbon arcs, mercury lamps, Xenon lamps, metal halide lamps, fluorescent lightings, tungsten lamps and argon ion lasers, for instance.

The artificial teeth used in the present invention are not specifically limited, and may be any one of porcelain, acrylic and polyurethane teeth put on the market and having general quality suitable for artificial teeth.

The artificial teeth may take on various forms such as tapering, square, ovoid, square-tapering, short-square, vigorous-square and vigorous-square-tapering forms, assume various color tones such as Bioblend color tones 102, 104, 106, 108, 112, 114, 116 and 118 and Vita color tones A, B, C and D, and be usually of sizes represented by the width of 6 anterior teeth of 30 to 50 mm and the width of 8 posterior teeth of 55 to 75 mm.

When it is desired to provide additional supply of the photopolymerizable resin used with the material pack according to the present invention, it may be filled in a separate syringe, from which it may taken and additionally used, as occasion demands.

BRIEF DESCRIPTION OF THE DRAWINGS

The material packs for preparing plate dentures according to the present invention will now be explained particularly but not exclusively with reference to the drawings.

Of the drawings,

More specifically, FIG. 3 illustrates an example in which a lid shown at 4 is provided over the photopolymerizable resin previously placed on the matrix portion formed of the light-transmitting material, as shown in FIG. 2, while taking into account the thickness of the denture, and FIG. 4 is an end face view taken along the line A—B of FIG. 3.

Figure 3:
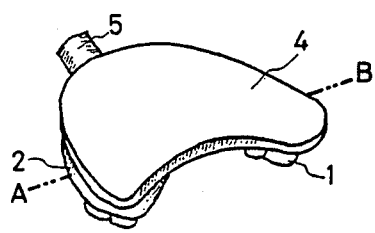
FIGS. 3 and 4 each show the provision of a lid over the photopolymerizable resin placed on the upper-jaw matrix portion formed of the light transmitting material and having thereon an arrangement of artificial teeth, as illustrated in FIG. 2.
Figure 4:
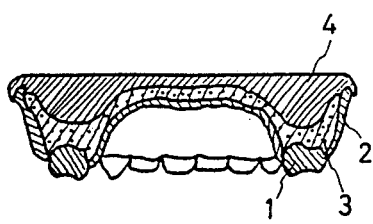

The active energy beams are irradiated on the photopolymerizable resin shown at 3 in FIG. 4 through the opening shown at 5 in FIG. 3 for the polymerization thereof.

Figure 5:
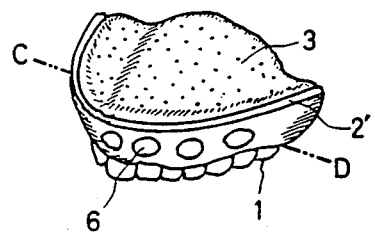

FIG. 5 illustrates another example in which a coating formed of a light shielding material is applied over the outside of the matrix with no provision of any lid, and the thus applied coating is partly removed from the outside of the matrix to form an opening for the admission of active energy beams.

Figure 6:
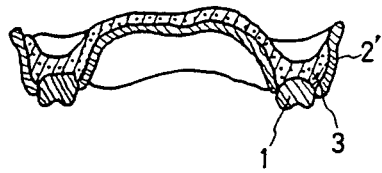

FIG. 6 is an end face view taken along the line C-D of FIG. 5, wherein reference numeral 2' shows a matrix formed of a light transmitting material coated on the outside with a light shielding material, and reference numeral 6 indicates an opening or cut-out formed by partial removal of the light shielding coating from the outside of the matrix, through which the active energy beams are irradiated on the photopolymerizable resin shown at 3 in FIG. 6 for its polymerization.

Figure 7:
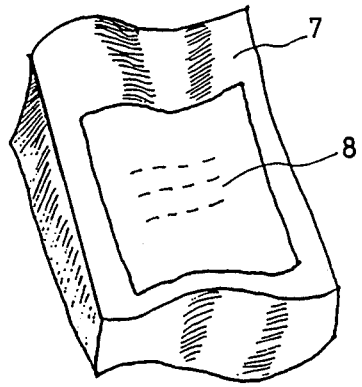

FIG. 7 is a perspective view showing one material pack for the preparation of denures according to the present invention.

In any case, the artificial teeth, matrix and photopolymerizable resin are sealed or packed in the outer package, shown in FIG. 7, to provide the material pack of the present invention. It is to be understood that the outer pack, shown at 7, in FIG. 7 may be formed any suitable light shielding material. Used to this end is any material capable of shielding incidental light such as, for instance, a plastic or glass material containing a light-shielding material or coated therewith. It is also to be appreciated that, since the contents table, shown at 8 in FIG. 7, on the surface of the outer pack formed of the material capable of shielding active energy beams specifies the required particulars including the size and form of the jaws, the size, form and color tne of artificial teeth and the color tone of photopolymerizable resins, it is possible to easily and surely select the matrix of the size and form accommodative to an individual, the artificial teeth of the color tone, form and size accommodative to an individual and the photopolymerizable resin of the color tone accommodative to an individual without unpacking the material pack of the present invention for the purpose of the confirmation of its contents.

EXAMPLES

The present invention will now be explained in further detail with reference to the following non-restrictive examples.

EXAMPLE 1

Figure 1:
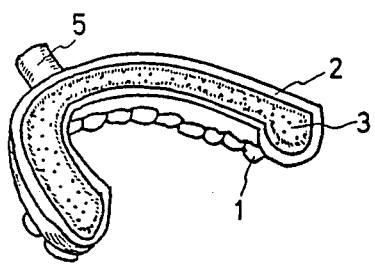
FIG. 1 is a perspective view showing a photopolymerizable resin placed on a lower-jaw matrix portion formed of a light transmitting material and having thereon an arrangement of artificial teeth.
Figure 2:
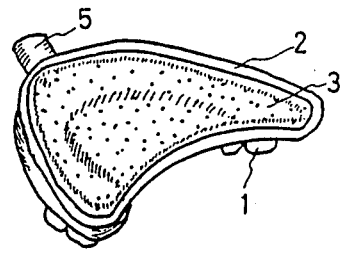
FIG. 2 is a perspective view showing a photopolymerizable resin placed on an upper-jaw matrix portion formed of a light transmitting material and having thereon an arrangement of artificial teeth, wherein reference numeral 1 indicates the artificial teeth in color tone, and of form and size accommodative to an individual; 2 stands for a matrix formed of a light transmitting material; 3 denotes a photopolymerizable resin; 5 represents an opening for the admission of active energy beams.

(1) Molds to make matrix such forms as shown in FIGS. 1 and 2 were prepared based on various gypsum models previously obtained from a plurality of intra-mouth forms and generally according to the size classification—extra small, small, medium, large, extra large—and the form classification—tapering, square and ovoid form—of the jaws.

(2) With the molds, an ionomer resin excelling in light transmission properties (manufactured by Mitsui-Du Pont Polychemical Co., Ltd. and available under the trade name of HI . MILAN) was inject-molded to make a plurality of matrixes provided with such active energy beam-irradiation openings as shown in FIGS. 1 and 2.

(3) Artificial teeth were set and arranged on the obtained matrixes. The artificial teeth were selected from any combination of seven forms—tapering, square, ovoid, tapering-square, short square, vigorous-tapering and vigorous-tapering-square forms—, eight color tones—Bioblend color tones 102, 104, 106, 108, 112, 114, 116 and 118, eleven kinds of anterior teeth arranged at an interval of 2 mm in the width of 6 anterior teeth of arrangement of 30 to 50 mm, and eleven kind of posterior teeth arranged at an interval of 2 mm in the width of 8 posterior teeth of arrangement of 55 to 75 mm.

(4) A layer of the photopolymerizable resin having the following composition was placed on the inside of each matrix having an arrangement of artificial teeth, and the photopolymerizable resin was placed on the inside of each matrix shown in FIGS. 1 and 2 and having thereon an arrangement of artificial teeth. The resulting products were placed in the outer plastic packs capable of shielding active energy beams.

(5) Specified on the contents table annexed to the outer pack were the form and size of the jaws, the size, form and color tone of the artificial teeth and the color tone of the photopolymerizable resin in connection with the matrix packed in the outer pack, having thereon an arrangement of the artificial teeth and provided on the inside with the photopolymerizable resin.

The photopolymerizable resin used in Example 1 had the composition as listed below.

2,2-bis[4-)2-hydroxy-3-methacryloxyphenyl)]propane: 70 g
Triethylene glycol dimethacrylate: 30 g
Camphor quinone: 1 g
Dimethylaminoethyl methacrylate: 0.5 g
Polymethyl methacrylate: 10 g
Finely divided silica treated with gamma-methacryloxy-propyl trimethoxy silane: 50 g

EXAMPLE 2

(1) Molds to make matrix such a form as shown in FIG. 5 were prepared based on various gypsum models previously obtained from a plurality of intra-mouth forms and generally according to the size classification—extra small, small, medium, large, extra large—and the form classification—tapering, square and ovoid form—of the jaws.

(2) With the molds, an ionomer resin excelling in light transmission properties (manufactured by Mitsui-Du Pont Polychemical Co., Ltd. and available under the trade name of HI . MILAN) was inject-molded to make a plurality of matrixes as shown in FIG. 5.

(3) A mask was applied over the portion of each matrix to provide later an active energy beam-irradiation opening. Thereafter, the light-shielding material or silver was coated or deposited on the outside of the matrix, as shown in FIG. 5.

(4) Artificial teeth were set and arranged on the obtained matrixes. The artificial teeth were selected from any combination of seven forms—tapering, square, ovoid, tapering-square, short square, vigorous-tapering and vigorous-tapering-square forms—, eight color tones—Bioblend color tnes 102, 104, 106, 108, 112, 114, 116 and 118, eleven kinds of anterior teeth arranged at an interval of 2 mm in the width of 6 anterior teeth of arrangement of 30 to 50 mm, and eleven kinds of posterior teeth arranged at an interval of 2 mm in the width of 8 posterior teeth of arrangement of 55 to 75 mm.

(5) A layer of the photopolymerizable resin having the following composition was placed on the inside of each matrix having an arrangement of artificial teeth, and the photopolymerizable resin was placed on the inside of the matrix shown in FIG. 5 and having thereon an arrangement of artificial teeth. The resulting products were put in the outer plastic packs capable of shielding the active energy beams.

(6) Specified on the contents table annexed to each outer pack were the form and size of the jaws, the size, form and color tone of the artificial teeth and the color tone of the photopolymerizable resin in connection with the matrix packed in the outer pack, having thereon an arrangement of artificial teeth and provided on the inside with the photopolymerizable resin.

The photopolymerizable resin used in Example 2 had the composition as stated below.

2,2-bis(4-methacryloxypolyethoxyphenyl)propane: 100 g
Methyl methacrylate polymer: 200 g
Camphor quinone: 0.2 g
Triethanolamine: 0.5 g
Benzoyl peroxide: 1.0 g

EXAMPLE 3

With the material packs for preparing plate dentures obtained in Example 1, the plate dentures were prepared according to the following procedures.

(1) An intra-mouth impression was taken with a silicone impression material. Gypsum slurry was poured into the obtained impression, and was set to prepare a gypsum model.

(2) Out of a number of the material packs for preparing plate dentures, the material pack accommodative to an objective individual in connection with the size and form of the jaws, the size, form and color tone of the artificial teeth and the color tone of the photopolymerizable resin was selected on the basis of the contents table born thereon.

(3) The contents of the selected pack were pressed against the gypsum model, and were trimmed out. Fine adjustment of the artificial teeth with respect to the antagonist's teeth was then made by moving the artificial teeth.

(4) Immediately upon such fine adjustment, visible rays were irradiated on the photopolymerizable resin (shown at 3) through the active energy beam-irradiation opening (shown at 5) for 3 minutes with a visible ray irradiator (manufactured by GC Dental Industrial Corp. and available under the table name of GC Light VL-1) for its polymerization.

(5) The matrix (shown at 2) comprising the light transmitting material deposited on the polymer was removed to obtain a plate denture.

(6) The peripheries of said plate denture were treated by grinding and polishing in the conventional manner.

The time required for preparing the plate denture was about 40 minutes, and the plate denture was available on the day it was prepared.

Available was also the plate denture of the form, color tone and size accommodative to an individual, unlike the conventional temporary denture comprising a combination of a temporary plate having thereon a temporary arrangement of artificial teeth with a self-curing resin.

EXAMPLE 4

With the material packs for preparing plate dentures obtained in Example 2, the plate dentures were prepared according to the following procedures.

(1) An intra-mouth impression was taken with a silicone impression material. Gypsum slurry was poured into the obtained impression, and was set to prepare a gypsum model.

(2) Out of a number of the material packs for preparing dentures, the material pack accommodative to an objective individual in connection with the size and form of the jaws, the size, form and color tone of the artificial teeth and the color tone of the photopolymerizable resin was selected on the basis of the contents table born thereon.

(3) The contents of the selected pack were pressed against the gypsum model, and were trimmed out. Fine adjustment of the artificial teeth with respect to the antagonist's teeth was then made by moving the artificial teeth.

(4) Immediately upon such fine adjustment, visible rays were irradiated on the photopolymerizable resin (shown at 3) through the active energy beam-irradiation opening shown at 6 for 3 minutes with a visible ray irradiator (manufactured by GC Dental Industrial Corp. and available under the trade name of GC Light VL-1) for its polymerization, said opening being provided on the outside of the matrix (shown at 2') formed of the light-transmitting material coated thereon with the light-shielding material.

(5) The matrix (shown at 2') comprising the light-transmitting material coated thereon with the light-shielding material and deposited on the cured product was removed to obtain a plate denture.

(6) The peripheries of said plate denture was treated by grinding and polishing in the conventional manner.

COMPARISON EXAMPLE 1

With a thermally polymerizable resin, a plate denture was prepared by the following steps.

(1) A preliminary impression of the oral mouth was taken with an alginate impression material.

(2) Gypsum slurry was poured into said impression to make a gypsum model.

(3) A self-curing resin (manufactured by GC Dental Industrial Corp. and available under the trade name of Ostron) was pressed against said gypsum model to make an individual tray.

(4) The individual tray was tried in the oral mouth, and was adjusted by means of a stamp bar.

(5) A rubber base impression material (manufactured by GC Dental Industrial Corp. and available under the trade name of Surflex F) was placed on the impression side of the individual tray to obtain a functional impression.

(6) The individual tray having said functional impression was boxed therearound with wax, followed by pouring of gypsum slurry, thereby obtaining a working model.

(7) Said working model was regulated with a model trimmer.

(8) A bite plate was made on said working model with paraffin wax.

(9) Said bite plate was tried in the oral mouth for bite taking.

(10) The bite plate used for bite taking and the working model were attached to an articulator.

(11) Artificial teeth were arranged on the bite plate on the articulator to prepare a wax denture.

(12) Said wax denture was tried and regulated in the oral mouth.

(13) Wax was placed on the gingival portion of said wax denture for formation of the gingival portion.

(14) The wax denture was put in a flask, and was invested in investment gypsum (manufactured by GC Dental Industrial Corp. and available under the trade name of Advastone).

(15) The wax denture invested in said gypsum was washed out in a wax washing out bath.

(16) A resin separator was applied on the gypsum surface.

(17) The powder and liquid components of the thermally polymerizable resin (manufactured by GC Dental Industrial Corp. and available under the trade name of Acron) were mixed together into a dough product.

(18) The dough resin was filled and pressed in a space defined by washing out of the invested gypsum.

(19) The invested gypsum filled therein with said thermally polymerizable resin was placed in a thermal polymerization device for thermal polymerization.

(20) The polymerized resin was removed from the gypsum.

(21) Gypsum deposited onto the polymerized resin denture was removed with an electric engine.

(22) The polymerized resin was ground and polished in the conventional manner to obtain a plate denture.

COMPARISON EXAMPLE 2

With a self-curing resin, a plate denture having a temporary arrangement of artificial teeth on a temporary plate was prepared by the following steps.

(1) The temporary plate having a temporary arrangement of artificial teeth was pressed against a gypsum model obtained according to the intra-formed of the oral mouth, and various adjustments were carried out.

(2) After such adjustments, a self-curing resin (manufactured by GC Dental Industrial Corp. and available under the trade name of Rebaron) was placed on the inside of the temporary plate having a temporary arrangement of artificial teeth, and was attached to an object, the impression of which was to be taken. Afterwards, the matrix was trimmed for the subsequent impression taking.

(3) The temporary plate having a temporary arrangement of artificial teeth was removed from the object, and the self-curing resin was allowed to set.

(4) The matrix portion was removed from the temporary plate having a temporary arrangement of artificial teeth, followed by grinding and polishing in the conventional manner, thereby obtaining a temporary denture.

The time required for preparing such a temporary denture was about 60 minutes.

It is to be noted that, since the artificial teeth were fixed in place, they could not be adjusted with respect to the antagonist's teeth, and so had unsatisfactory occlusal relation thereto.

Since the size types of the temporary plates each having a temporary arrangement of artificial teeth are limited, it was impossible to obtain any denture accommodative to the oral mouth of an individual.

The artificial teeth themselves were ready-made, and were not expected to be accommodative to the form, color tne and size of any individual. In other words, it was impossible to obtain any temporary denture which met even one of accommodativeness to the peculiarity of an individual, excellent fitting accuracy and satisfactory aesthetics of appearance.

The plate dentures and temporary dentures for the same individual were prepared according to the procedures of Examples 3 and 4 and Comparison Examples 1 and 2. The fitting accuracy of the prepared plate dentures and temporary dentures was estimated by placing a silicone base fitting test material (manufactured by GC Dental Industrial Corp. and available under the trade name of Fit Checker) on the mucosal surfaces thereof, and trying them in the oral mouth to measure the amount of the test material deposited thereon. The appearance of the prepared dentures and temporary dentures was observed and estimated in terms of how much they showed a natural tooth and gingival state. The preparation time of the plate dentures and temporary dentures were that needed for preparing them according to the procedures of Examples 3 and 4 and Comparison Examples 1 and 2.

TABLE 1

|  | Fitting Accuracy | Aesthetics of Appearance | Preparation Time |
| --- | --- | --- | --- |
| Ex. 3 | good | excellent | 40 min. |
| Ex. 4 | good | excellent | 40 min. |
| Comp. Ex. 1 | fairly good | excellent | 900 min |
| Comp. Ex. 2 | bad | bad | 60 min. |

From the results of Table 1, it is clear that the plate dentures having more improved fitting accuracy and aethetics of appearance could be prepared within a very short time of about 40 minutes with the material packs of Examples 3 and 4. The preparation of plate dentures with the material packs according to the present invention does not rely upon the conventional indirect process generally carried out so as to obtain dentures having good fitting accuracy and aethetics of appearance, which involves a number of steps such as the reproduction of the intra-mouth state on a working model, the formation of a wax denture and the replacement of the wax denture by a resin, as is the case with the preparation of plate dentures with the thermally polymerizable resin shown in Comparison Example 1. In other words, the preparation of plate dentures according to the present invention relies upon a direct process by which plate dentures having more improved fitting accuracy and aethetics of appearance can be obtained within a very short time. As shown in Comparison Example 2, the self-curing resin used with the temporary plate having a temporary arrangement of artificial teeth varies in setting time with the temperature, e.g., room temperature, applied during manipulation, and should be handled, while paying attention to the setting time during impression taking. In addition, setting of such a resin tends to start prematurely, so that sufficient impression taking is not achievable.

In this respect, the photopolymerizable resin used with the material pack according to the present invention is not set, unless it is exposed to visible rays. Thus, according to the present invention, satisfactory results are obtained by taking a sufficiently precise impression of the objective for impression taking and, thereafter, irradiating it with visible rays for about 3 minutes.

Further, there is no fear that the matrix (shown at 2 and 2') of the material pack may be deformed by the heat of reaction, and the degree of shrinkage upon polymerization is reduced or limited. For these reasons, the plate dentures having more improved fitting accuracy can be obtained. In addition, out of a number of artificial teeth bearing resemblance in form, color tone and size to the natural teeth, the most accommodative ones can be selected as the artificial teeth to be used with the material pack according to the present invention. Thus, it is possible to obtain the plate denture having its appearance more improved.

The artificial teeth project at their tips from the matrix (shown at 2 and 2'), and can thus be adjusted with respect to the antagonist's teeth. Hence, the plate denture having improved occlusal relation can be obtained.

According to the present invention, the matrix (shown at 2) may be provided with the lid (shown at 4) for the purpose of protecting the photopolymerizable resin placed inside of the matrix so as to make optimum the thickness to define the plate therefor.

What is claimed is:

1. A material pack for the preparation of plate dentures, comprising an outer pack formed of a material capable of shielding active energy beams, said outer pack containing therein: (1) a matrix formed of a light transmitting material, (2) a photopolymerizable resin provided inside of said matrix, and (3) artificial teeth provided on said matrix while a part thereof projects from said matrix into said photopolymerizable resin such that said artificial teeth are finely adjustable; and wherein the necessary particulars including, the size and form of said matrix, the size, form and color tone of said artificial teeth and the color tone of said photopolymerizable resin are specified on said outer pack.

2. A material pack as defined in claim 1, in which said matrix is coated thereon with a material capable of shielding active energy beams.

* * * * *